(12) United States Patent
Goodin

(10) Patent No.: US 6,955,099 B2
(45) Date of Patent: Oct. 18, 2005

(54) SPILL PROOF LIQUID SAMPLE CUP

(76) Inventor: John W. Goodin, 31941 Via Oso, Coto De Caza, CA (US) 92679

(*) Notice: Subject to any disclaimer, the term of this patent is extended or adjusted under 35 U.S.C. 154(b) by 19 days.

(21) Appl. No.: 10/624,878

(22) Filed: Jul. 21, 2003

(65) Prior Publication Data
US 2004/0060374 A1 Apr. 1, 2004

Related U.S. Application Data

(60) Provisional application No. 60/397,572, filed on Jul. 19, 2002.

(51) Int. Cl.[7] ............................................. G01N 1/12
(52) U.S. Cl. ............................ 73/864.51; 73/864.65
(58) Field of Search ........................ 73/864.51, 864.63, 73/864.65; 422/55–58, 61, 99; 436/164–170

(56) References Cited

U.S. PATENT DOCUMENTS

| 4,827,944 A | | 5/1989 | Nugent |
|---|---|---|---|
| 5,119,830 A | | 6/1992 | Davis |
| 5,316,732 A | | 5/1994 | Golukhov et al. |
| 5,403,551 A | * | 4/1995 | Galloway et al. ............. 422/58 |
| 5,403,830 A | | 4/1995 | Place |
| 5,429,804 A | | 7/1995 | Sayles |
| 5,595,187 A | | 1/1997 | Davis |
| 5,849,505 A | | 12/1998 | Guirguis |
| 6,074,606 A | | 6/2000 | Sayles |
| 6,277,646 B1 | * | 8/2001 | Guirguis et al. ............ 436/165 |
| 6,342,183 B1 | | 1/2002 | Lappe et al. |
| 6,361,744 B1 | * | 3/2002 | Levy ........................... 422/99 |
| 6,375,897 B1 | | 4/2002 | Bachand |
| 6,403,383 B1 | | 6/2002 | Casterlin et al. |
| 6,576,193 B1 | * | 6/2003 | Cui et al. ..................... 422/58 |
| 6,616,893 B1 | * | 9/2003 | Pham ......................... 422/58 |
| 6,786,106 B2 | * | 9/2004 | Alley ...................... 73/864.51 |

* cited by examiner

Primary Examiner—Charles Garber
(74) Attorney, Agent, or Firm—Knobbe, Martens, Olson & Bear, LLP

(57) ABSTRACT

A spill proof liquid sample cup is provided having an outer shell and an inner liner. The inner liner defines a sample chamber. The inner liner is spaced inwardly from the outer shell such that a test chamber is formed between the outer shell and the inner liner that is fluidly separate from the sample chamber. The inner liner is configured with a valve to allow selective fluid communication between the sample chamber and the test chamber. The valve is actuatable by either removing a bottom cap, manual manipulation, or by an external tool. One or more test strips are located within the test chamber to provide information about the sample fluid.

21 Claims, 4 Drawing Sheets

SPILL PROOF LIQUID SAMPLE CUP

CROSS REFERENCE TO RELATED APPLICATIONS

The present application claims priority to U.S. Provisional Application having Ser. No. 60/397,572, filed on Jul. 19, 2002, the entire contents of which is hereby incorporated by reference.

BACKGROUND OF THE INVENTION

1. Field of the Invention

The present invention relates to the field of liquid sample cups. More specifically, a spill proof sample cup that allows incorporation of data strips and selective exposure of the sample fluid to the data strips to provide information about the liquid sample.

2. Description of the Related Art

Liquid sample cups are provided for a variety of uses. For example, such uses include pH balance testing, chemical testing, drug testing, and other such uses where the unknown constituents contained in a solution are of interest.

One typical method of obtaining the desired information is by using well-known data test strips. Test strips are strips of material treated with a substance designed to detect and display the presence of certain markers within the solution.

For example, drug test strips are configured to detect and display the presence of certain drugs in a body fluid sample. Typically, drug testing is performed on a urine sample.

One desired feature of such a liquid sample cup is the ability to seal the sample and inhibit it from spilling out of the cup. In addition, it is desirable to conduct certain types of testing at specific temperatures. In the case of body fluid sampling, the test is designed to be performed within a predetermined amount of time after the body fluid sample has been obtained and allowed to sufficiently cool. Furthermore, some tests require that the results be read and recorded within a specified amount of time after the fluid sample contacts the test strip. Therefore, it is preferable that the exposure of the test strip to the fluid sample is selectively controlled such that the test strip and fluid sample are kept separate until it is desired to run the test.

In many prior art sample cups, the isolation of the test strip from the fluid sample is obtained by utilizing separate containers, or by later opening the sample cup and introducing the test strips to the sample cup at an appropriate time. However, there is always a risk of spillage or contamination when a sample cup is subsequently opened to either transfer the contents or to subsequently introduce a test strip.

SUMMARY OF PREFERRED EMBODIMENTS OF THE INVENTION

Accordingly, embodiments of the present invention provide a sample cup that is both substantially spill proof and maintains separation between the fluid sample and the test strips until it is desired to expose the test strips to the sample fluid.

According to one embodiment, a liquid sample cup has a rigid outer substantially annular shell defining an open top, a bottom, an inside and an outside. An inner liner is disposed within the outer shell and has an open top, a bottom having a flow aperture formed therein, an inside and an outside. The inner liner defines a sample chamber. Further, the outside of the inner liner cooperates with the inside of the outer shell to provide a test chamber. A plug is configured to selectively fluidly seal the flow aperture. A seal cap is also provided and configured to seal the outer shell open top.

According to other embodiments, the seal cap has an access hole formed therein. Additionally, a screw-on cap can be provided to seal the open top of the outer shell. The plug can extend from the bottom of the outer shell inwardly such that it sealingly engages the flow aperture. The plug can be displaced from the flow aperture manually, by interaction with a removable bottom cap, or by an external tool. One or more test strips can be provided within the test chamber.

According to another embodiment, a liquid sample cup comprises a generally annular outer shell, an annular inner liner having an interior defining a sample chamber and carried by the outer shell and having a portion spaced inwardly therefrom such that a test chamber is formed between the outer shell and the inner liner. A data test strip is located within the test chamber.

Additional embodiments allow selective fluid communication between the sample chamber and the test chamber. The inner liner can incorporate a valve configured to allow selective communication between the sample chamber and the test chamber. The valve can include a plug seat formed in the inner liner. A plug can be formed on the bottom of the outer shell and configured to provide a fluid tight seal between the sample chamber and the test chamber when engaged with the plug seat. A bottom cap can be provided and configured to engage the plug and selectively displace the plug from the plug seat, thereby allowing fluid communication between the sample chamber and the test chamber. In some embodiments, the bottom cap is threadably engaged with the outer shell and is configured such that an unscrewing of the bottom cap from the outer shell displaces the plug from the plug seat. The bottom cap can include a ball configured to mate with a semi-spherical impression in the plug. The plug can be additionally be configured to be displaced from the plug seat manually or by an external tool

DETAILED DESCRIPTION OF THE PREFERRED EMBODIMENT

In the following description, reference is made to the accompanying drawings which form a part of this written description which show, by way of illustration, specific embodiments in which the invention can be practiced. It is to be understood that other embodiments may be utilized and structural changes may be made without departing from the scope of the present invention. Where possible, the same reference numbers will be used throughout the drawings to refer to the same or like components. Numerous specific details are set forth in order to provide a thorough understanding of the present invention; however, it should be obvious to one skilled in the art that the present invention may be practiced without the specific details or with certain alternative equivalent devices and methods to those described herein. In other instances, well-known methods, procedures, components and devices have not been described in detail so as not to unnecessarily obscure aspects of the present invention.

Figure 1:
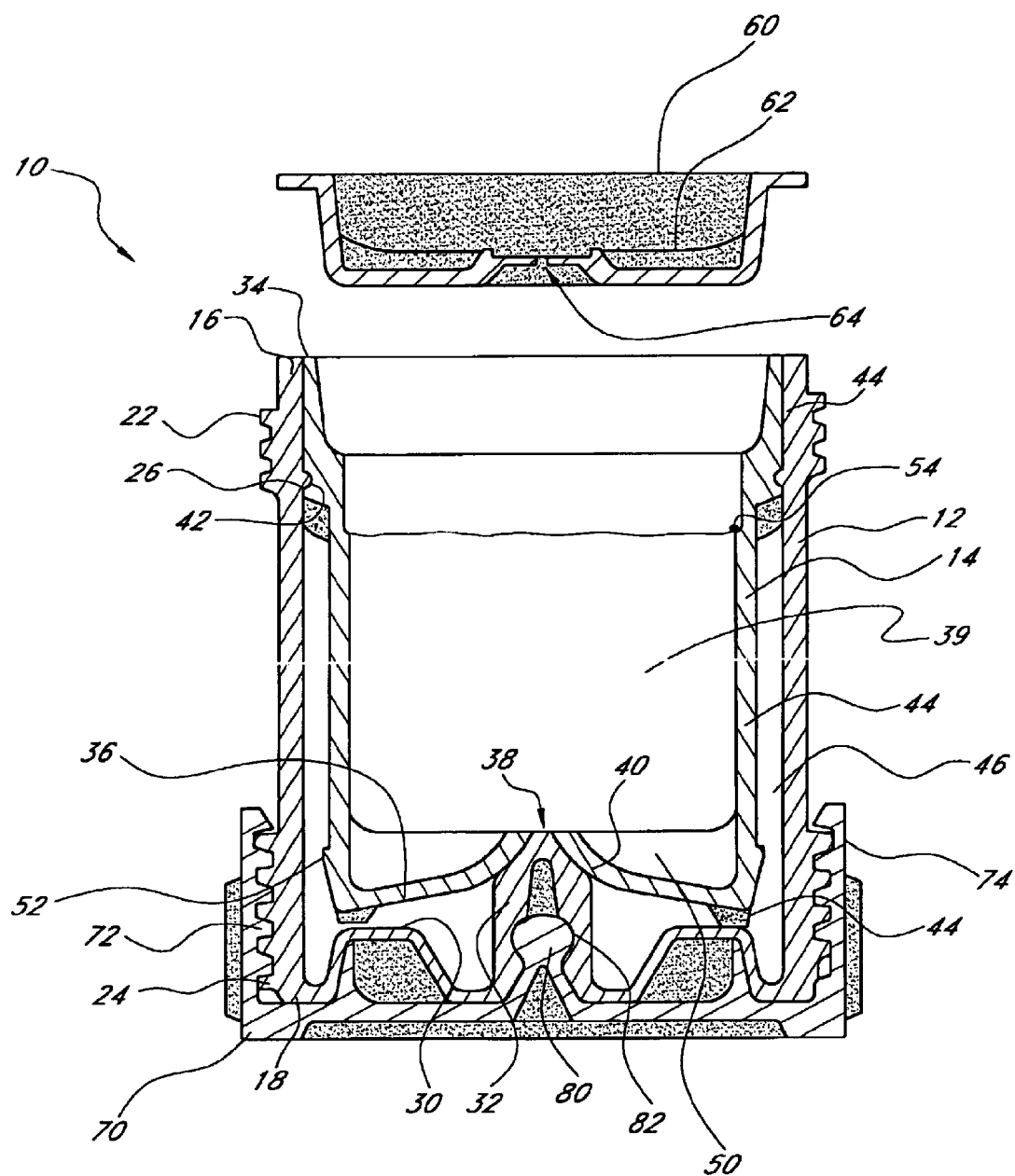
FIG. 1 illustrates a cross-sectional elevational view of one embodiment of a liquid sample cup.

FIG. 1 illustrates a sample cup having an outer shell 12 and an inner liner 14. The outer shell is generally annular in shape. As used herein, the term "annular" is a broad term. In some instances, it is used to denote a continuous, closed, peripheral shape such as, for example, a cylinder, an extruded square, rectangle, oval, or other regular or non-regular geometric shape capable of forming a fluid container.

The outer shell 12 is preferably substantially rigid such that it holds its shape and resists moderate deforming forces associated with stacking, shipping, and handling of the sample cup 10. The outer shell 12 has a top 16 and a bottom 18. In one embodiment, addition, some embodiments incorporate outer lower threads 24 formed toward the outer shell bottom 18.

A circumferential bead 26 is formed around the inside surface of the outer shell 12 toward the top, which purpose will be described later. The outer shell 12 bottom 18 is preferably configured with a support shelf 30 and a plug 32. In the illustrated embodiment, the plug 32 includes a substantially conical section, as will be described below.

The outer shell 12 is preferably formed of a transparent or semi-transparent material. In some embodiments, a suitable polymer is preferred. Polymers are preferred for their ease of manufacturing and ability to accept various enhancers into the liquid mix prior to part formation. Examples of suitable enhancers are color additives, plasticisers, additives that increase the materials resistance to certain chemicals, and other additives that increase the materials ability to be used as described herein. The outer shell is preferably manufactured by a suitable molding process, although other techniques can be used by those of ordinary skill in the art.

In one embodiment, the inner liner 14 is annular in shape and is carried by the outer shell 12. As illustrated, the inner liner 14 is cylindrical and is the preferred shape for ease of manufacturing and because it is conducive for having threads. The inner liner 14 includes a top 34 and a bottom 36. The top 34 is preferably open and thus, the inner liner 14 defines a sample chamber 39 therein. The bottom 36 includes a flow aperture 38 and a plug seat 40 around the flow aperture 38. The plug seat 36 may be any suitable shape; however, as illustrated, one embodiment incorporates a plug seat 36 formed frustroconically and thereby suitably adapted to receive a substantially conical plug 32.

A circumferential groove 42 is formed toward the top 34 of the inner liner 14 and is configured to mate with the circumferential bead 26 of the outer shell 12 to connect the two components together and form a substantially fluid tight seal therebetween. The fluid tight seal is further enhanced by surface contact friction barrier 44 between an upper portion of the inner liner 14 and an upper portion of the outer shell 12.

The inner liner 14 is preferably formed of similar materials and techniques as the outer shell 12. Like the outer shell 12, the inner liner 14 is preferably transparent or translucent to allow a visual inspection of the fluid contents therein.

During assembly of the device, which may be performed at any suitable time, such as during manufacture or just prior to sample collection, the inner liner 14 is inserted into the outer shell 12 until the circumferential bead 26 enters and engages the circumferential groove 42. Preferably, the outer shell 12 elastically deforms to allow the circumferential bead 26 to fit over the inner liner 14. As such, when the circumferential bead 26 engages the circumferential groove 42, an audible and tactile pop will alert the assembler that the pieces are in proper engaging relationship. Of course, other engaging structure can be incorporated to provide the desired features.

The inner liner 14 is configured with recessed sidewall portion 44 spaced inwardly from the outer shell 12. The cooperation of the recessed sidewall portion 44 and the outer shell 12 define a test chamber 46 between the inner liner 14 and the outer shell 12.

Upon assembly of the inner liner 14 and the outer shell 12, the plug 32 seals against the plug seat 40 and the two components cooperate to provide a fluid tight seal between the sample chamber 39 and the test chamber 46.

The inner liner 14 is further configured with one or more feet on its bottom 36 which are positioned to rest on the support shelf 30 once assembled. In this way, the assembled relative position between the inner liner 14 and outer shell 12 is encouraged thereby maintaining the seal between the plug 32 and the plug seat 40.

The inner liner 14 is further configured with one or more internal ribs 50 disposed radially along its bottom 36. The ribs 50 not only provide increased stiffness to the inner liner 14, but also serve as splash control to reduce the tendency of a sample liquid from splashing up and out of the sample cup 10 during sampling.

In some embodiments, the inner liner 14 is configured with a circumferential rib 52 around its outer periphery toward its bottom 36. This rib 52 can be used to provide a rough level of flow control, as will be described below. Finally, the inner liner 14 can have any sort of visual cues, such as graduated volumetric markings, or a maximum fluid level marking 54. The visual cues can be formed during manufacture, such as by forming a groove or raised rib. Alternatively, the visual cues may be later added, such as by applying a colorant to the surface or by adhering a sticker or any suitable way of adding visual cues.

A seal insert 60 is configured to fit within the upper portion of the inner liner 14 and to provide a fluid seal therewith. In the illustrated embodiment, the seal insert 60 is bowl-shaped; however, other configurations are possible and will provide the benefits and functions described herein, as will be apparent to one of ordinary skill in the art. In some embodiments, the seal insert 60 forms a friction fit with the inner liner 14. In other embodiments, a mechanical coupling, such as a threaded engagement, for example, may be provided to secure the components together and provide a fluid tight seal. Alternatively, a circumferential bead and groove combination can be used to secure the seal insert 60 into the inner liner 14.

The seal insert 60 may have one or more stiffening ribs 62 to provide added rigidity to the sidewall that engages the inner liner 14. A breather hole 64 may be provided in the seal insert 60 for various reasons. For example, the air trapped within the sample cup can escape as the seal insert 60 is inserted into the inner liner 14 thereby reducing the internal pressure of the sample cup. Additionally, the breather hole 64 allows limited access to the interior of the sample cup, such as for a pipette to enter and retrieve a small sample while limiting the risk of spillage or contamination of the fluid sample within the sample cup 10.

In one preferred embodiment, the seal insert 60 is formed of soft polyethylene and is sized and shaped to frictionally fit within the inner liner 14 and to provide a substantially fluid tight seal therewith.

A bottom cap 70 is secured to the bottom of the sample cup 10, such as through a threaded engagement. In the illustrated embodiment, the outer shell 12 includes lower threads 24 formed around the outer periphery thereof. The bottom cap 70 has mating threads 72 formed on its internal periphery and can therefore be detached from the outer shell 12 by unscrewing the bottom cap 70 from the outer shell 12. However, in some embodiments, it is preferable that the bottom cap 70 only be removed at a specified time during the sample collection and testing and additional retaining structure can be provided to inhibit inadvertent removal of the bottom cap 70.

For example, in one embodiment, the bottom cap 70 includes a tamper evident seal, such as a tear ring 74. Thus, a technician can verify that the bottom cap 70 has not yet been removed from the outer shell 12 by visual inspection of the tear ring for reasons discussed below. Where a tear ring 74 is provided, the tear ring 74 is manually removed from the bottom cap 70 before the cap is able to be removed from the outer shell 12. This can be accomplished by manually pulling on the tear ring 74 to tear it along a pre-scored line of weakness to dislocate the tear ring 74 from the bottom cap 70. Alternatively, simply unthreading the bottom cap 70 from the outer shell 12 can cause the tear ring 74 to be separated from the bottom cap 70, thereby allowing the bottom cap 70 to be removed from the outer shell 12.

In some embodiments, the bottom cap 70 is configured with a projection 80 configured to mate with a corresponding recess 82 in the outer shell 12. In the illustrated embodiment, the bottom cap 70 is configured with a bead 80 and the outer shell 12 is configured with a semi-spherical recess 82 configured to receive the bead 80. It is preferable that the connection between the projection 80 and recess 82 allows the projection 80 to rotate relative to the recess 82. The illustrated connection is merely examplary, and any suitable configuration of connection is possible without departing from the scope herein. Such alternative embodiments could include an annular bead and a cooperating groove. Those of skill in the art will realize that other suitable structure is capable of providing the described features without departing from the scope hereof.

Figure 2:
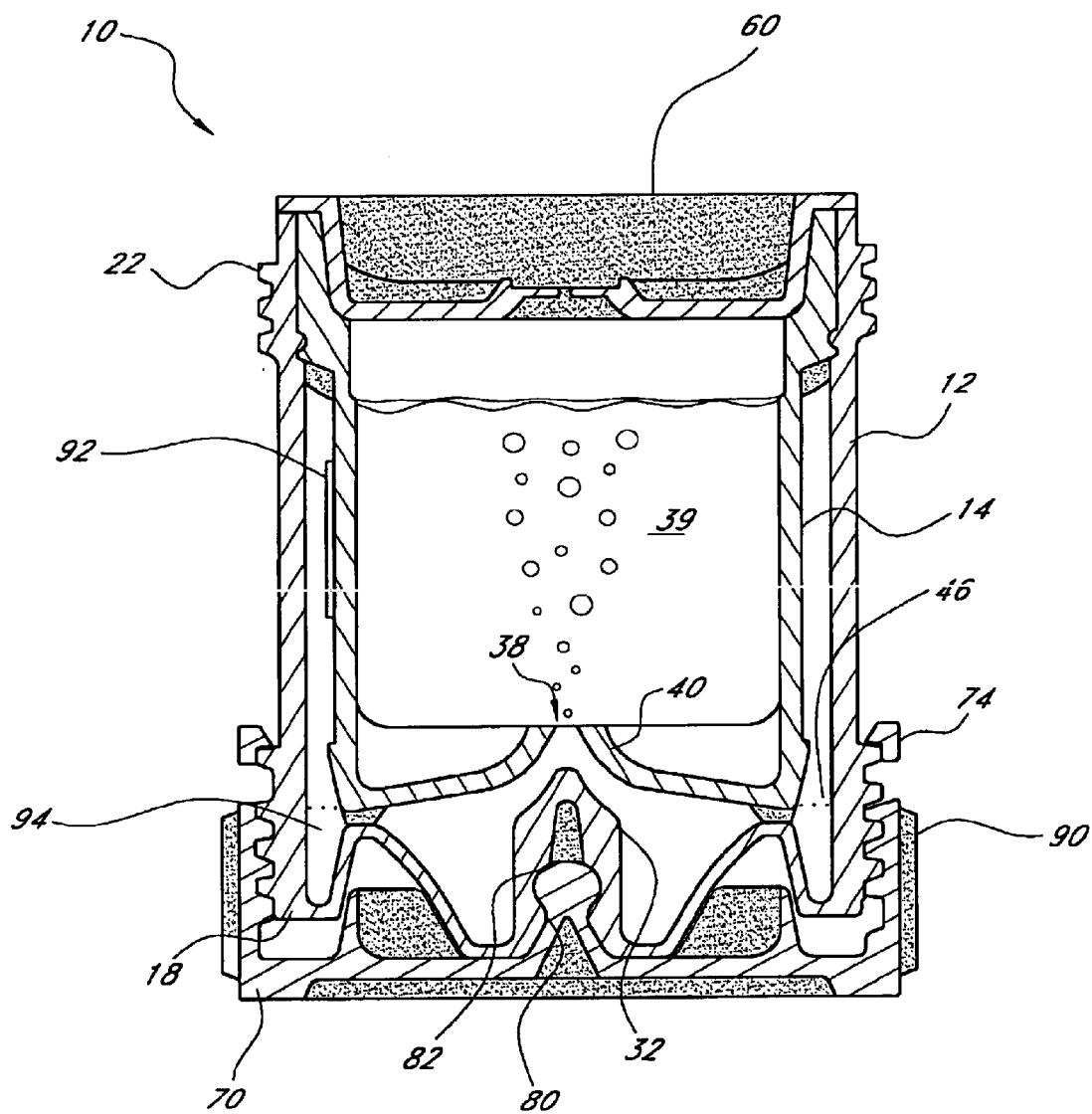
FIG. 2 illustrates a cross-sectional elevational view of the embodiment of the liquid sample cup showing the seal cap attached to the top of the cup.

With reference to FIG. 2, the use of the sample cup 10 is illustrated. Once a fluid sample is introduced into the sample cup 10, either the donor, or a technician inserts the seal insert 60 to substantially seal the sample cup 10. The bottom cap 70 is then removed from the bottom of the outer shell 12. The tear ring 74 can either be manually removed prior to manipulation of the bottom cap 70, or can be removed as a result of manipulating the bottom cap 70.

As the bottom cap 70 is being removed, the projection 80 will exert a force on the recess 82 which causes the plug 32 to withdraw from the plug seat 40. This may result in resistance to removal of the bottom cap 70. Accordingly, the bottom cap 70 may be configured with raised ribs or knurling to allow an increased gripping and rotating force.

As the plug 32 withdraws from the plug seat 40, the sample chamber 39 is in fluid communication with the test chamber 46 through the flow aperture 38. At this time, the fluid sample is free to flow through the flow aperture 38 and into the test chamber 46. There will likely be a volume of air within the test chamber 46 that will be compressed as the fluid sample fills the test chamber 46. As such, the volume of fluid sample that enters the test chamber 46 is controlled by the balancing pressure forces of the fluid pressure resulting from the column of fluid within the sample chamber 39 with the air pressure from within the test chamber 46 in combination with the fluid column pressure of the sample fluid in the test chamber 39. Accordingly, the sample cup 10 can be designed to control the fluid column height within the test chamber.

Upon full removal of the bottom cap 70 from the outer shell 12, the projection 80 exits the recess 82 and the plug 32 snaps back into sealing engagement with the plug seat 40. Once the bottom cap 70 is fully removed, it may be affixed to the top of the cup by threadably engaging the bottom cap 70 with the upper threads 22 of the outer shell 12. Alternatively, the bottom cap 70 may be discarded and another cap can be used to seal the top of the sample cup 10.

Preferably during manufacture, one or more test strips 92 are affixed to the sample cup 10. The test strips 92 may include any of a wide variety of test strips configured to detect and display any of a wide variety of substances within the fluid sample. In some embodiments, test strips 92 may be incorporated that test for the presence of specific drugs. Those of skill in the art will readily realize the wide variety of test strips that can be incorporated into the sample cup disclosed herein. Other types of information-displaying test strips 92 can be incorporated, such as temperature indicating test strips.

Where a temperature indicating test strip is utilized, it is preferable to locate it in close proximity to the sample chamber such that the sample temperature may be obtained before the sample is allowed to flow into the test chamber 46. Accordingly, a temperature indicating test strip can be adhered or otherwise affixed directly to the inner liner 14, and may be attached either to the inside or the outside of the inner liner 14.

Other test strips can be affixed to either the inner liner 14 or the outer shell 12 within the test chamber 46 and by configuring the test strips 92 to extend down toward the outer shell bottom 18 (denoted by the reference numeral 94), they will be wetted by the sample fluid within the test chamber 46. The outer shell 12 can be optionally configured with internal longitudinal ribs (not shown) to separate each test strip. These are beneficial in those embodiments where the test strips are not affixed within the test chamber 46, and the longitudinal ribs can be used to orient the test strips within the test chamber 46. In addition, the longitudinal ribs increase the rigidity of the sample cup 10 and provide increased crush resistance.

As discussed above, it is preferable that both the outer shell 12 and inner liner 14 are substantially transparent so that the level of fluid and the information displayed by the test strips 92 can be visually obtained.

Figure 3:
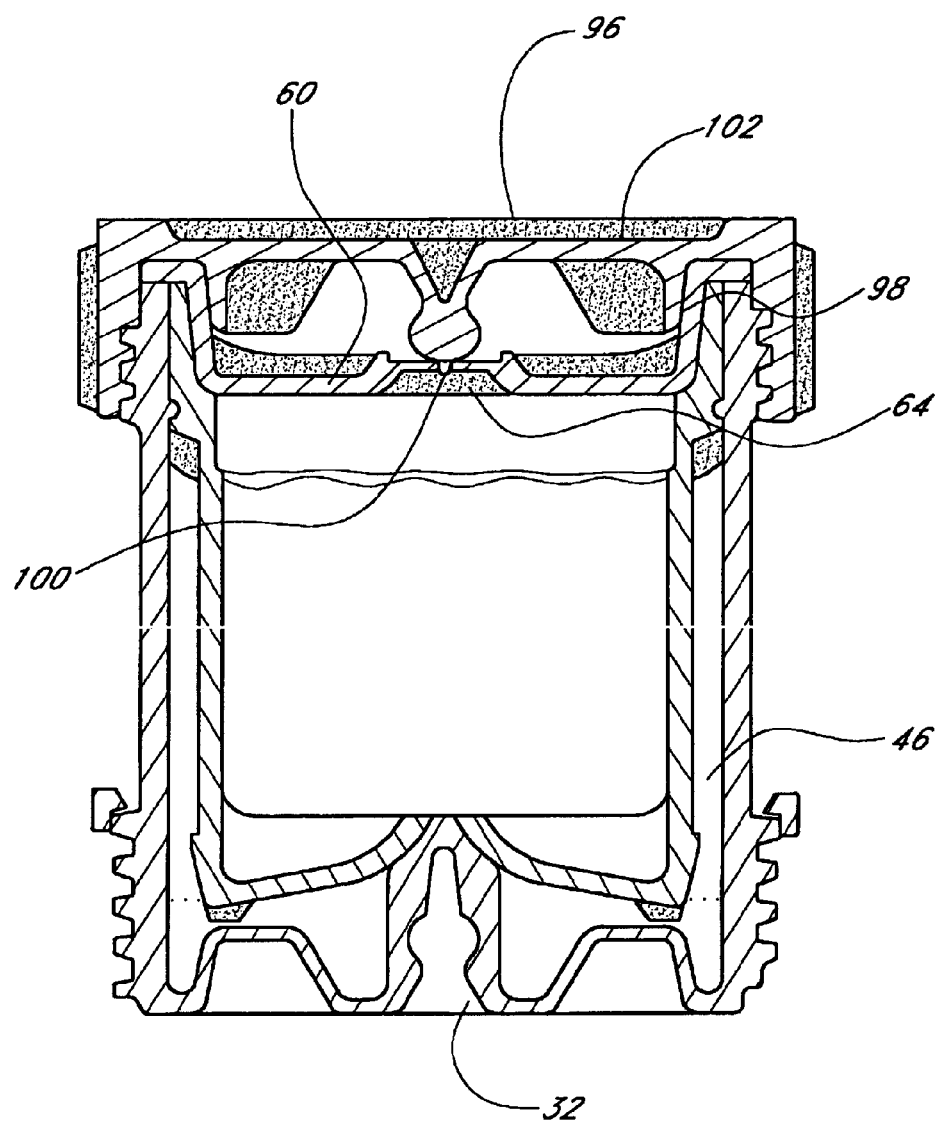
FIG. 3 illustrates a cross-sectional view of one embodiment of a liquid sample cup showing the bottom cap removed and a cap secured to the top.
Figure 4:
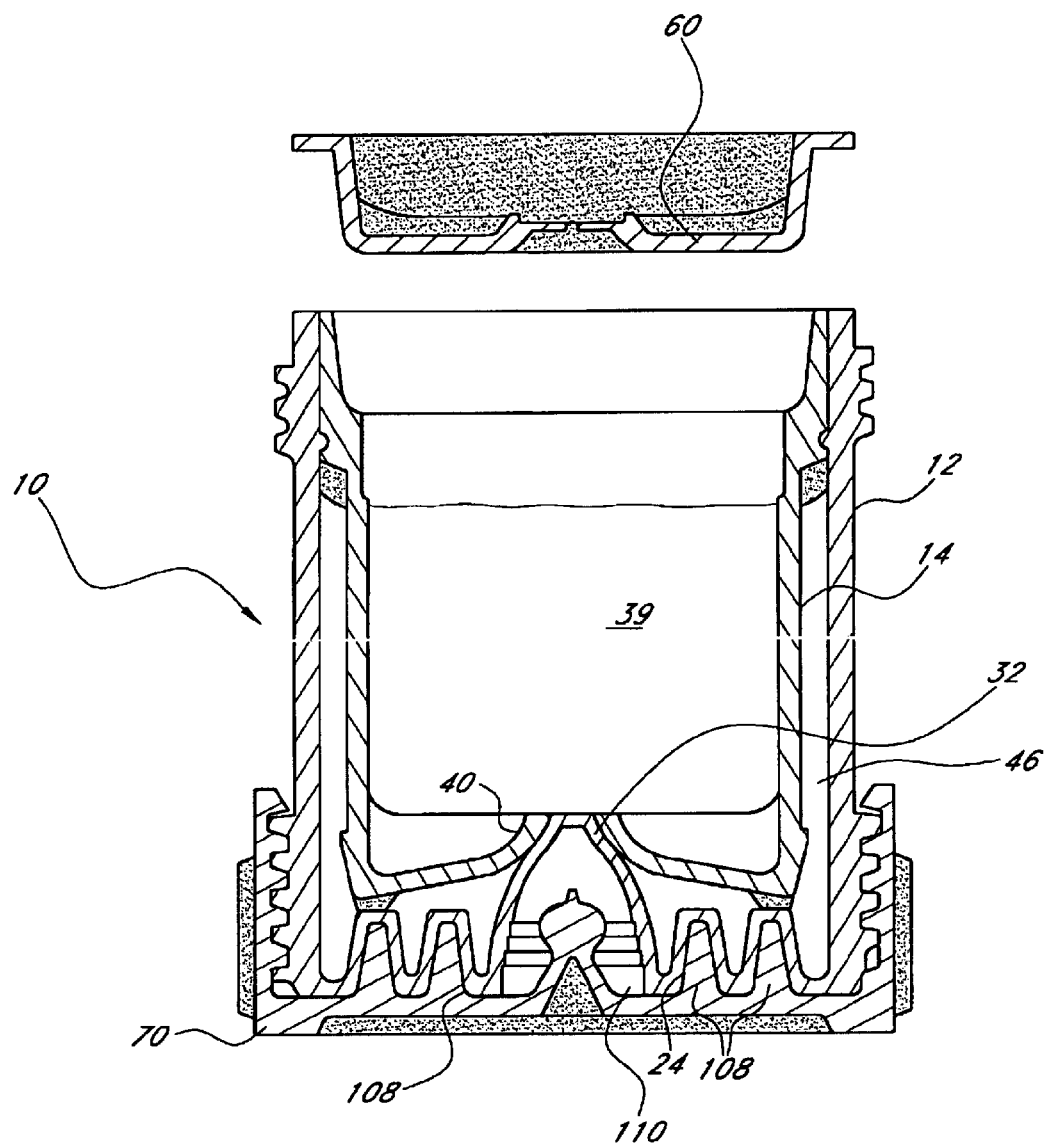
FIG. 4 illustrates a cross-sectional view of another embodiment of a liquid sample cup having a manually actuatable valve.

With reference to FIG. 3, it can be seen that the bottom cap 70, or another cap, (both now referred to generally as top cap 96 when in the position illustrated by FIG. 4), can be affixed to the top of the sample cup 10. The top cap 96 is preferably configured to cooperate with suitable retaining structure on the outer shell 12. As illustrated, a threaded engagement is provided to secure the top cap 96 onto the outer shell 12 to thereby fluidly seal the sample cup 10. Additional structure, such as one or more pressure flanges 98, are provided to the top cap 96 to provide an increased pressure against the seal insert 60 thereby increasing the seal between the seal insert 60 and the inner liner 14 as the top cap 96 is affixed to the outer shell 12.

In addition, the top cap 96 can be configured with a stopper 98 to seal the breather hole 64 once the top cap 96 is securely attached to the outer shell 12. Thus, the sample fluid is securely contained within the sample chamber 39 and the test chamber 46 and is inhibiting from flowing through the breather hole 64.

The top cap 96 is further configured with a dedicated area to receive a tamper evident adhesive strip. In one embodiment, the top cap 96 is configured with a smooth set down 102 that spans the top of the top cap 96 and provides an area for an adhesive strip to adhere. The tamper evident adhesive strip is provided to not only provide a tamper evident cue, but to also contain information, such as chain of custody information. Of course, other desirable information can be displayed on the adhesive strip, such as the sample date and time, as well as information about the sample donor.

With reference to FIG. 4, one possible alternative embodiment is illustrated that utilizes many of the principles already disclosed herein. A sample cup 10 includes an outer shell 12 and an inner liner 14 as previously described. The embodiment of FIG. 4 mainly differs in the actuation of the plug 32.

The inner liner 14 is configured with a similar plug seat 40 as previously described. A plug 32 is provided that sealingly engages the plug seat 40; however, the illustrated plug differs from the embodiments previously disclosed by incorporating a hollow cone seal. The plug 32 is urged against the plug seat 32 by ridges 108 on the bottom cap 70 that impart a force against the outer shell bottom 24.

After removal of the bottom cap 70, a technician can manually release the seal of the plug 32 against the plug seat 40 by inserting a finger into the hollow 110 and displacing the plug 32 sideways to deform the plug seat 44 thereby allowing fluid communication between the sample chamber 39 and the test chamber 46.

There are several fluid sample tests that are required to be performed on fluids within a specific temperature range. For body fluids, this typically means that a technician must wait for a given time after receiving the sample before the test can be performed to allow fluid to cool to within the necessary temperature range. In addition, some fluid sample test strips must be read within a certain amount time after the test strip has been exposed to the fluid sample. Since these two time periods can be vastly different, the disclosed embodiments provide a sample test cup that maintains the sample fluid separate from the test chamber and integrated test strips. Preferably, many embodiments disclosed herein provide a temperature indication test strip to display the temperature of the sample fluid. Upon visual inspection of the temperature indication test strip through the outer shell and in some embodiments, through the inner liner, the technician can determine when the fluid sample is within the necessary temperature range to perform the desired tests.

The technician intentionally allows the sample fluid to flow into the test chamber by manipulating the plug thereby releasing its seal with the plug seat. This can be done in any of a number of disclosed ways. For example, embodiments disclosed herein teach that the plug can be manipulated by interaction with a bottom cap. The bottom cap can have a releasable connection with the plug, and by manipulating the displacing the bottom cap, the plug is displaced from the plug seat thereby allowing the sample fluid to flow into the test chamber. Alternatively, the plug can be manually manipulated, such as by a technician dislodging it from the plug seat by pushing on it directly. Other embodiments can provide for a more secure release of the plug from the plug seat by requiring an external tool to actuate the release. For example, a wrench or driver can be required to manipulate the plug. In addition, the table-mounted tool may be provided and the sample cup can be placed on top of the tool and then rotated to dislodge the plug from the plug seat. Of course, those of skill in the art will realize that there are many other structures and methods of selectively exposing one or more test strips to a fluid sample.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A liquid sample cup, comprising:
   a rigid outer substantially annular shell defining an open top, a bottom, an inside and an outside;
   a substantially annular inner liner disposed within the outer shell and having an open top, a bottom having a flow aperture therein, an inside and an outside, the inner liner defining a sample chamber therein, the cooperation of the inside of the outer shell and the outside of the inner liner defining a test chamber;
   a seal cap configured to seal the inner liner open top; and
   a plug configured to selectively fluidly seal the flow aperture in the inner liner, wherein the plug is capable of selectively sealing and unsealing the flow aperture while the seal cap is positioned so as to seal the inner liner open top.

2. The liquid sample cup of claim 1, wherein the seal cap has an access hole formed therein.

3. The liquid sample cup of claim 1, further comprising a screw-on cap configured to seal the open top of the outer shell.

4. The liquid sample cup of claim 1, wherein the plug extends from the bottom of the outer shell inwardly such that it sealingly engages the flow aperture.

5. The liquid sample cup of claim 4, wherein the plug is configured to be displaced from a sealing engagement by manual displacement.

6. The liquid sample cup of claim 4, wherein the plug is configured to be displaced from a sealing engagement by an interaction with a removable bottom cap.

7. The liquid sample cup of claim 6, wherein the seal cap has an access hole formed therein and the removable bottom cap is configured to engage the open top of the outer shell so as to fluidly seal the access hole.

8. The liquid sample cup of claim 4, wherein the plug is configured to be displaced from a sealing engagement by an external tool.

9. The liquid sample cup of claim 1, further comprising one or more data test strips located within the test chamber.

10. The liquid sample cup of claim 1, wherein the plug is capable of selectively sealing and unsealing the flow aperture while the seal cap is off such that the inner liner open top is open.

11. A liquid sample cup, comprising:

a rigid outer substantially annular shell defining an open top, a bottom, an inside and an outside;

a substantially annular inner liner disposed within the outer shell and having an open top, a bottom having a flow aperture therein, an inside and an outside, the inner liner defining a sample chamber therein, the cooperation of the inside of the outer shell and the outside of the inner liner defining a test chamber;

a plug configured to selectively fluidly seal the flow aperture in the inner liner, wherein the plug extends from the bottom of the outer shell inwardly such that it sealingly engages the flow aperture, and wherein the plug is configured to be displaced from a sealing engagement by an interaction with a removable bottom cap; and a seal cap configured to seal the inner liner open top.

12. A liquid sample cup, comprising:

a rigid outer substantially annular shell defining an open top, a bottom, an inside and an outside;

a substantially annular inner liner disposed within the outer shell and having an open top, a bottom having a flow aperture therein, an inside and an outside, the inner liner defining a sample chamber therein, the cooperation of the inside of the outer shell and the outside of the inner liner defining a test chamber;

a plug configured to selectively fluidly seal the flow aperture in the inner liner, wherein the plug extends from the bottom of the outer shell inwardly such that it sealingly engages the flow aperture, and wherein the plug is configured to be displaced from a sealing engagement by an external tool; and a seal cap configured to seal the inner liner open top.

13. A liquid sample cup comprising:

a generally annular outer shell having an outer surface;

a generally annular inner liner having an interior defining a sample chamber and carried by the outer shell and having a portion spaced inwardly therefrom such that a test chamber is formed between the outer shell and the inner liner;

a valve comprising a plug seat formed in the inner liner;

a plug formed on the bottom of the outer shell and configured to provide a fluid tight seal between the sample chamber and the test chamber when engaged with the plug seat; and a bottom cap configured to engage the plug when engaged with a lower portion of the outer surface of the outer shell, wherein the bottom cap is further configured to selectively displace the plug from the plug seat while being disengaged from the outer shell, thereby allowing fluid communication between the sample chamber and the test chamber.

14. The sample cup of claim 13, wherein the plug is configured to re-engage the plug seat after the bottom cap has been disengaged from the outer shell, thereby fluidly resealing the valve.

15. The sample cup of claim 13, further comprising a data test strip located within the test chamber.

16. The sample cup of claim 13, wherein the bottom cap includes a projection configured to mate with a cooperating impression in the plug.

17. The sample cup of claim 13, wherein the plug is configured to be displaced from the plug seat by manual actuation.

18. The sample cup of claim 13, wherein the plug is configured to be displaced from the plug seat by an external tool.

19. A liquid sample cup comprising:

a generally annular outer shell;

a generally annular inner liner having an interior defining a sample chamber and carried by the outer shell and having a portion spaced inwardly therefrom such that a test chamber is formed between the outer shell and the inner liner, wherein the sample chamber is in selective fluid communication with the test chamber, wherein the inner liner incorporates a valve configured to allow selective communication between the interior of the inner liner and the cavity, wherein the valve comprises a plug seat formed in the inner liner;

a data test strip located within the test chamber;

a plug formed on the bottom of the outer shell and configured to provide a fluid tight seal between the sample chamber and the test chamber when engaged with the plug seat; and a bottom cap configured to engage the plug and selectively displace the plug from the plug seat, thereby allowing fluid communication between the sample chamber and the test chamber, wherein the bottom cap is threadably engaged with the outer shell and is configured such that an unscrewing of the bottom cap from the outer shell displaces the plug from the plug seat.

20. The liquid sample cup of claim 19, wherein the bottom cap includes a projection configured to mate with a cooperating impression in the plug.

21. The liquid sample cup of claim 19, wherein the plug is configured to be displaced from the plug seat by an external tool.

* * * * *

UNITED STATES PATENT AND TRADEMARK OFFICE
CERTIFICATE OF CORRECTION

| | | |
|---|---|---|
| PATENT NO. | : 6,955,099 B2 | Page 1 of 1 |
| APPLICATION NO. | : 10/624878 | |
| DATED | : October 18, 2005 | |
| INVENTOR(S) | : Goodin, John W. | |

It is certified that error appears in the above-identified patent and that said Letters Patent is hereby corrected as shown below:

At Column 3, Line 18, after "embodiment," insert -- the outer shell 12 has upper threads 22 formed on its outer periphery near the top 16. In --.

Signed and Sealed this

Eighth Day of August, 2006

JON W. DUDAS
*Director of the United States Patent and Trademark Office*